(12) United States Patent
Toyama et al.

(10) Patent No.: US 8,241,916 B2
(45) Date of Patent: Aug. 14, 2012

(54) DIAGNOSTIC METHOD FOR OIL-FILLED ELECTRICAL APPARATUS

(75) Inventors: Satoru Toyama, Chiyoda-ku (JP); Junji Tanimura, Chiyoda-ku (JP); Hisakatsu Kawarai, Chiyoda-ku (JP); Tsuyoshi Amimoto, Chiyoda-ku (JP)

(73) Assignee: Mitsubishi Electric Corporation, Tokyo (JP)

( * ) Notice: Subject to any disclaimer, the term of this patent is extended or adjusted under 35 U.S.C. 154(b) by 1 day.

(21) Appl. No.: 12/677,323

(22) PCT Filed: Apr. 16, 2008

(86) PCT No.: PCT/JP2008/057400
§ 371 (c)(1),
(2), (4) Date: Mar. 10, 2010

(87) PCT Pub. No.: WO2009/054155
PCT Pub. Date: Apr. 30, 2009

(65) Prior Publication Data
US 2010/0192673 A1     Aug. 5, 2010

(30) Foreign Application Priority Data
Oct. 26, 2007   (JP) ................................ 2007-278754

(51) Int. Cl.
*G01N 33/28* (2006.01)
*G01N 30/02* (2006.01)
*G01N 30/72* (2006.01)

(52) U.S. Cl. ............ 436/120; 436/60; 436/61; 436/119; 436/140; 436/161; 436/173

(58) Field of Classification Search .............. 436/60–61, 436/119–120, 140, 161, 173
See application file for complete search history.

(56) References Cited

U.S. PATENT DOCUMENTS
4,280,894 A * 7/1981 Taylor ............................ 208/15
(Continued)

FOREIGN PATENT DOCUMENTS
JP          5 315147       11/1993
(Continued)

OTHER PUBLICATIONS

Fleming, S. A. et al, Journal of Organic Chemistry 1996, 61, 7040-7044.*
Qiu, C, et al, Industrial and Engineering Chemistry Research 2005, 44, 4151-4155.*
Toyama, S. et al, IEEE Transactions on Dielectrics and Electrical Insulation 2009, 16, 509-515.*

(Continued)

*Primary Examiner* — Arlen Soderquist
(74) *Attorney, Agent, or Firm* — Oblon, Spivak, McClelland, Maier & Neustadt, L.L.P.

(57) ABSTRACT

A method allowing an accurate diagnosis of a failure of an oil-filled electrical apparatus resulting from production of copper sulfide even with a small amount of an insulating oil is implemented. A diagnostic method for an oil-filled electrical apparatus for diagnosing a failure of the oil-filled electrical apparatus having a copper part disposed in an insulating oil is implemented by detecting at least one compound of bibenzyl and dibenzyl sulfide in the oil of the oil-filled electrical apparatus, to diagnose a failure of the oil-filled electrical apparatus in accordance with the detected amount of the compound. It is configured such that a failure of the oil-filled electrical apparatus resulting from production of copper sulfide can be diagnosed by detecting a specified substance, which allows an accurate diagnosis of a failure even with a small amount of the insulating oil.

5 Claims, 4 Drawing Sheets

U.S. PATENT DOCUMENTS

| | | | | |
|---|---|---|---|---|
| 4,430,205 | A | * | 2/1984 | Felsky .......................... 208/246 |
| 4,542,246 | A | * | 9/1985 | Matsunaga et al. ............ 585/6.6 |
| 4,755,275 | A | * | 7/1988 | Sato et al. ....................... 208/14 |
| 2007/0197405 | A1 | * | 8/2007 | Holmes et al. ................ 508/110 |

FOREIGN PATENT DOCUMENTS

| | | |
|---|---|---|
| JP | 7 335446 | 12/1995 |
| JP | 8 124751 | 5/1996 |
| JP | 9 72892 | 3/1997 |
| JP | 2000 241401 | 9/2000 |
| JP | 2002 350426 | 12/2002 |
| JP | 2005 223104 | 8/2005 |
| JP | 2008-224514 | 9/2008 |

OTHER PUBLICATIONS

Van Hamme, et al., "Dibenzyl Sulfide Metabolism by White Rot Fungi", Applied and Environmental Microbiology, vol. 69, No. 2, pp. 1320-1324, Feb. 2003.

Scatiggio, et al., "Understanding and Management fo Sulfur Corrosion from Insulating Oil", Doble Engineering Company—74th Annual International Doble Client conference, pp. 1-13, 2007.

Yang, et al., "Simultaneous determination of phenols (bibenzyl, phenanthrene, and fluorenone) in Dendrobium species by high-performance liquid chromatography with diode array detection", Journal of Chromatography A, 1104 (2006), pp. 230-237, 2006.

* cited by examiner

| COMPOUND | COMPOUND FORMULA | DISCOLORATION (PRODUCTION OF COPPER SULFIDE) |
|---|---|---|
| HEXYL MERCAPTAN | C7H13SH | NOT DISCOLORED |
| DIHEXYL SULFIDE | C7H13SC7H13 | NOT DISCOLORED |
| DIHEXYL DISULFIDE | C7H13SSC7H13 | NOT DISCOLORED |
| HEXYL THIOPHENE | C4H5SC7H13 | NOT DISCOLORED |
| BENZYL MERCAPTAN | C6H5CH2SH | DISCOLORED |
| DIBENZYL SULFIDE | C6H5CH2SCH2C6H5 | SLIGHTLY DISCOLORED |
| DIBENZYL DISULFIDE | C6H5CH2SSCH2C6H | DISCOLORED |
| DIBENZYL SULFOXIDE | C6H5CH2SOCH2C6H5 | SLIGHTLY DISCOLORED |

DIAGNOSTIC METHOD FOR OIL-FILLED ELECTRICAL APPARATUS

TECHNICAL FIELD

The present invention relates to a method for diagnosing a failure occurring due to sulfidation corrosion of an oil-filled electrical apparatus.

BACKGROUND ART

There are some oil-filled electrical apparatuses such as an oil-filled transformer which may include an insulating oil containing a sulfur component. In this case, it is known that the sulfur component reacts with a copper part in the oil to produce copper sulfide exhibiting electrical conductivity, which leads to a problem that dielectric breakdown occurs. However, the details of the mechanism for producing copper sulfide are not known. Furthermore, it is difficult to diagnose a failure of the oil-filled electrical apparatus resulting from production of copper sulfide, without suspending the operation of the existing apparatus. Thus, the techniques for selecting an insulating oil suppressing sulfidation corrosion and for removing sulfur compounds are employed to reduce its tendency to produce copper sulfide.

For example, Japanese Patent Document 1 described below discloses a method for selecting an insulating oil which suppresses sulfidation corrosion. A certain amount of insulating oil and a copper plate having a predetermined surface area are enclosed in a container and heated at a predetermined temperature for a predetermined period of time. Then, the content percentages of the dissolved copper in the oil and sulfate ions contained in the insulating oil are measured to obtain the sum of the percentages, which is used to diagnose the sulfidation corrosiveness of the insulating oil.

Furthermore, a method for diagnosing a failure of an oil-filled electrical apparatus by detecting a certain type of substance is known. For example, Japanese Patent Document 2 described below discloses a method for diagnosing failures such as overheating or discharging within the apparatus based on whether or not there is detection of acetic acid [$CH_3COOH$], 3-pentanone [$CH_3CH_2COCH_2CH_3$], 2.5-dimethylfuran [$C_6H_8O$], butyraldehyde [$CH_3CHCHCHO$], 2-methoxyethanol [$C_3H_8O_2$], methanethiol [$CH_3SH$], dimethyl sulfide [$(CH_3)S_2$], ammonia [$NH_3$], 1.3-diazine [$C_4H_4N_2$], methyl vinylacetylene [$C_5H_6$], and 2-methyl-1.3-butadiene [$C_5H_8$] which are not detected from the oil-filled electrical apparatus during normal operation, but likely to be detected only when overheating or discharging occurs.

Furthermore, Japanese Patent Document 3 described below discloses a diagnostic method using the amount of each gas such as carbon dioxide [$CO_2$], carbon monoxide [$CO$], methane [$CH_4$], hydrogen [$H_2$], ethane [$C_2H_6$], ethylene [$C_2H_4$], and acetylene [$C_2H_2$] contained in the oil as an index showing the conditions including deterioration and failures of an oil-filled transformer, a reactor, an oil-filled electrical apparatus such as an automatic voltage regulator, an oil-immersed cable, and the like.

Furthermore, Japanese Patent Documents 4 and 5 described below each disclose a diagnostic method for an oil-filled transformer in which hydroxymethylfurfural and furfural are detected and used as an index of deterioration of the insulating paper.

Furthermore, Japanese Patent Document 6 described below discloses a method for detecting a sulfur compound and a product thereof in the oil in order to diagnose flow electrification of an oil-filled electrical apparatus.

Patent Document 1: Japanese Patent Laying-Open No. 07-335446

Patent Document 2: Japanese Patent Laying-Open No. 09-072892

Patent Document 3: Japanese Patent Laying-Open No. 2000-241401

Patent Document 4: Japanese Patent Laying-Open No. 05-315147

Patent Document 5: Japanese Patent Laying-Open No. 08-124751

Patent Document 6: Japanese Patent Laying-Open No. 2005-223104

DISCLOSURE OF THE INVENTION

Problems to be Solved by the Invention

In order to diagnose a failure of an oil-filled electrical apparatus resulting from production of copper sulfide by a sulfur component contained in the insulating oil of the oil-filled electrical apparatus and a copper part in the oil, the process of heating the copper plate and the insulating oil is required as disclosed in Patent Document 1, which involves a considerable amount of time and effort. In order to improve the diagnosis accuracy, a sufficient amount of insulating oil is also required for reacting the copper plate with the insulating oil. In addition, the diagnostic method for an oil-filled transformer implemented by detecting various substances is disclosed as in Patent Documents 2 to 6, which fails to allow diagnosis of a failure of the oil-filled electrical apparatus resulting from production of copper sulfide.

Thus, the present invention provides a method allowing an accurate diagnosis of a failure of the oil-filled electrical apparatus resulting from production of copper sulfide even when a small amount of insulating oil is employed.

Means for Solving the Problems

A diagnostic method for an oil-filled electrical apparatus according to the present invention provides a method for diagnosing a failure of the oil-filled electrical apparatus having a copper part disposed in an insulating oil. The diagnostic method includes the step of: detecting at least one compound of bibenzyl and dibenzyl sulfide in the insulating oil, and diagnosing a failure of the oil-filled electrical apparatus in accordance with a detected amount of the compound.

Effects of the Invention

It is configured such that a failure of the oil-filled electrical apparatus resulting from production of copper sulfide can be diagnosed by detecting a specified substance, which allows an accurate diagnosis of a failure even when a small amount of the insulating oil is employed. Accordingly, a diagnosis can be made using a small amount of insulating oil extracted from the existing oil-filled electrical apparatus, which facilitates diagnosis without the need to suspend the operation of the oil-filled electrical apparatus.

BEST MODES FOR CARRYING OUT THE INVENTION

First Embodiment

The oil-filled electrical apparatus to which a diagnostic method according to the present invention is applied includes a container containing an insulating oil and a copper part containing copper and copper alloy immersed in the insulating oil. For example, the oil-filled electrical apparatus is a transformer having a coil made of copper and insulating paper wound around the coil. Furthermore, the insulating oil is as defined in Japanese Industrial Standards (JIS) C 2320, for example.

Figure 1:
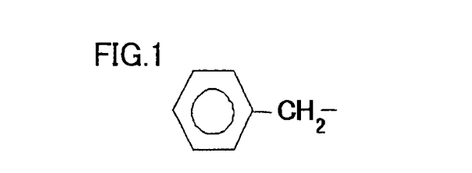
FIG. 1 is a structural formula of a part of a substance detected in accordance with a diagnostic method for an oil-filled electrical apparatus according to the first embodiment.

The diagnostic method for the oil-filled electrical apparatus according to the first embodiment provides a method for diagnosing the oil-filled electrical apparatus as having a failure by detecting a sulfur compound having sulfur bonded to a benzyl group, such as dibenzyl disulfide. FIG. 1 is a structural formula of a portion corresponding to a benzyl group bonded to the sulfur compound which is a substance to be detected by the diagnostic method for the oil-filled electrical apparatus according to the first embodiment. The details will be described below.

It is known that the insulating oil of the oil-filled electrical apparatus includes a component containing sulfur which reacts with copper to produce copper sulfide exhibiting electrical conductivity, leading to a problem that an insulation failure occurs. However, it is not known what kind of substance containing sulfur in the insulating oil exerts a significant influence on production of copper sulfide. Accordingly, it is considered that, if a substance exerting a significant influence on production of copper sulfide can be identified, only the substance is detected to thereby allow diagnosis of a failure of the oil-filled electrical apparatus resulting from production of copper sulfide. Thus, the following experiments were conducted.

Among various sulfur compounds contained in the insulating oil, hexyl mercaptan, dihexyl sulfide, dihexyl disulfide, hexyl thiophene, benzyl mercaptan, dibenzyl sulfide, dibenzyl disulfide, and dibenzyl sulfoxide were selected to examine the reactivity of these sulfur compounds with copper. First, these compounds each were dissolved in the alkylbenzene oil which is an insulating oil corresponding to an oil defined in JIS C 2320, class 2, No. 3, to prepare a sample oil. The dissolved amount of each compound was adjusted to achieve sulfur to have a mass concentration of 30 ppm at the point of time when each compound was dissolved. Then, 4 grams of each sample oil was weighed out and enclosed in the sample bottle having a volume of 10 $cm^3$. The gas phase portion enclosed together with each sample oil in the sample bottle was assumed to be air. Then, a copper plate (15 mm×20 mm, a thickness of 0.2 mm, approximately 0.5 grams) was placed in the sample bottle and immersed in the sample oil. The sample bottle was heated at 135° C. for 72 hours, and the reactivity with copper was evaluated based on the discoloration of the copper plate. It is to be noted that this discoloration results from production of copper sulfide, and stronger discoloration leads to a higher reactivity with copper, indicating that a greater amount of copper sulfide is produced.

Figure 2:
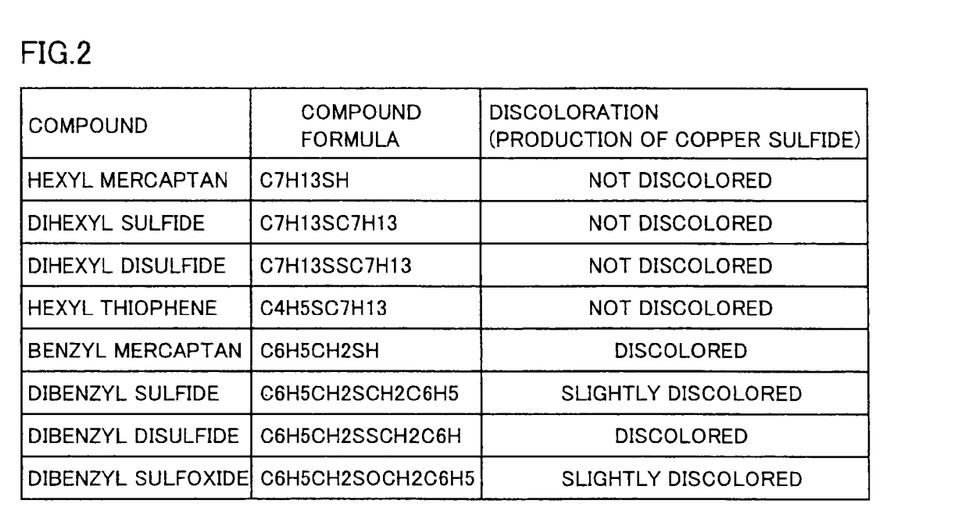
FIG. 2 is a table showing results of the experiment conducted for determining a diagnostic method for the oil-filled electrical apparatus according to the first embodiment.

FIG. 2 is a table showing the results of the experiment conducted for determining a diagnostic method for the oil-filled electrical apparatus according to the first embodiment. In each case of benzyl mercaptan and dibenzyl disulfide, the most significant discoloration occurs, and therefore, a greater amount of copper sulfide is produced. Furthermore, in each case of dibenzyl sulfide and dibenzyl sulfoxide, the discoloration also occurs, and copper sulfide is produced. On the other hand, it is found that discoloration scarcely occurs in each case of hexyl mercaptan, dihexyl sulfide, dihexyl disulfide and hexyl thiophene, which exert little influence on production of copper sulfide.

Hexyl mercaptan, dihexyl sulfide, dihexyl disulfide, and hexyl thiophene each are a sulfur compound having sulfur bonded to an alkyl group, and have little influence on production of copper sulfide. On the other hand, it is found that benzyl mercaptan, dibenzyl sulfide, dibenzyl disulfide, and dibenzyl sulfoxide each are a sulfur compound having sulfur bonded to a benzyl group, and thus, each have a relatively high reactivity with copper.

Therefore, when the sulfur compound having sulfur bonded to a benzyl group in the insulating oil is detected, it can be determined that the oil-filled electrical apparatus containing this insulating oil is likely to suffer an insulation failure caused by copper sulfide. Thus, with regard to the oil-filled electrical apparatus according to the first embodiment, a sulfur compound having sulfur bonded to a benzyl group is detected to diagnose a failure of the oil-filled electrical apparatus in accordance with the detected amount of the compound.

The method for detecting a sulfur compound in the insulating oil can be implemented, for example, by using gas chromatography-mass spectrometry (GC-MS). Since the substance to be detected is specified, detection can be made even if the amount of the insulating oil is small.

Figure 3:
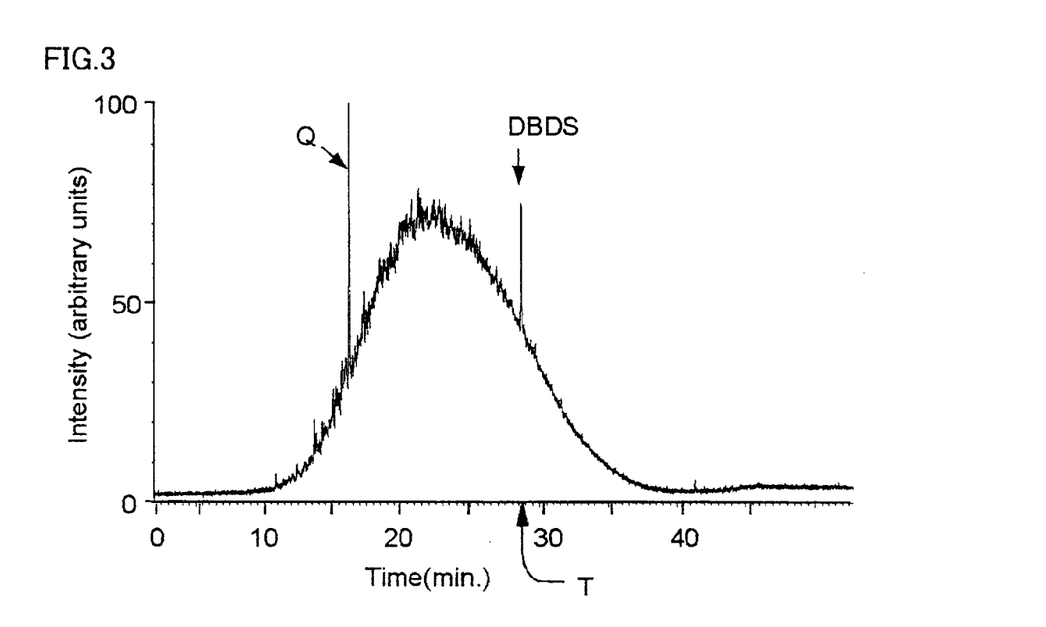
FIG. 3 is a graph showing an example of the diagnostic method for the oil-filled electrical apparatus according to the first embodiment.

FIG. 3 is a graph showing the measurement results of GC-MS which is an example of the means for detecting a sulfur compound in accordance with the diagnostic method for the oil-filled electrical apparatus according to the first embodiment. The figure shows a mass chromatogram obtained by measurement by GC-MS in the case where dibenzyl disulfide (hereinafter referred to as DBDS) is contained in the insulating oil composed of a mineral oil corresponding to an oil defined in JIS C 2320, class 1, No. 4. In the figure, the horizontal axis represents elapsed time since the introduction into the gas chromatography column, and the vertical axis represents a detection signal intensity. The vertical axis is represented on the basis that the value of the highest signal intensity is set at 100 in arbitrary units. As shown in the figure, when dibenzyl disulfide is contained in the insulating oil, a peak appears in the detection signal intensity of the mass-to-charge ratio of the benzyl group after a specific time T has elapsed since the insulating oil was introduced into the column. This specified time T corresponds to a time period varying with the substance and also depending on the measurement machine and measurement conditions. A peak Q appearing at the time before the peak of DBDS appears in the figure is caused not by the sulfur compound but by the substance irrelevant to the present invention. Furthermore, the broad signal overlapping peak Q and the peak of DBDS is a noise caused not by the sulfur compound but by the component contained in the mineral oil.

Accordingly, a small amount of insulating oil is extracted from the existing oil-filled electrical apparatus, to detect a sulfur compound having sulfur bonded to a benzyl group in the insulating oil by the detection method as described above. Thus, based on the amount of the detected compound, the oil-filled electrical apparatus can be diagnosed as having a failure or as having a high possibility of having a failure.

The diagnosis of a failure may be made based on the fact that a sulfur compound having sulfur bonded to a benzyl group is detected or the fact that the compound contains a specified concentration or more. In the case where the concentration of the sulfur compound having sulfur bonded to a benzyl group is very low, the influence is not significant enough to cause an insulation failure by copper sulfide depending on the structure of the oil-filled electrical apparatus. In other words, since the allowable concentration of each sulfur compound in the insulating oil depends on the insulation structure of the transformer, the specified concentration or more contained therein allows more accurate diagnosis.

The diagnostic method according to the first embodiment eliminates the need to measure in advance a sulfur compound in the insulating oil introduced into the oil-filled electrical apparatus, or to measure the temporal change of the amount of the sulfur compound. This facilitates the diagnosis for the existing oil-filled electrical apparatus.

In addition, with regard to the sulfur compound having sulfur bonded to a benzyl group in the unused insulating oil before introduced into the oil-filled electrical apparatus, the concentration of the sulfur compound may be measured, or the temporal change of the concentration of the sulfur compound may be measured. It is considered that each sulfur compound has been mixed at the time when the insulating oil is poured into the oil-filled electrical apparatus. If each sulfur compound is detected before the insulating oil is poured into the oil-filled electrical apparatus, the insulating oil mixed with the sulfur compound can be prevented in advance from being introduced into the oil-filled electrical apparatus. Furthermore, as described below, it is considered that each sulfur compound reacts with copper. Since it is considered that each sulfur compound decreases in accordance with production of copper sulfide, it is also possible to diagnose a failure by estimating the produced copper sulfide based on the concentration of each sulfur compound in the early stage and during use.

Second Embodiment

The diagnostic method for the oil-filled electrical apparatus according to the second embodiment is implemented by detecting at least one compound of bibenzyl and dibenzyl sulfide in the insulating oil and diagnosing a failure of the oil-filled electrical apparatus in accordance with the detected amount of the compound. The details will be described below.

When a sulfur compound having sulfur bonded to a benzyl group, such as dibenzyl disulfide, exists in the insulating oil, it reacts with copper to produce copper sulfide. If the compound generated during production of copper sulfide due to this reaction is detected, production of copper sulfide can be indirectly found, which was, however, not implemented since the details of the mechanism of copper sulfide production were conventionally unknown.

According to the study of the product formed by the reaction between copper and the sulfur compound having sulfur bonded to a benzyl group, it has been found that the reaction causes production of bibenzyl and dibenzyl sulfide. It is considered that this reaction mechanism starts with the reaction as the first stage in which the sulfur compound having sulfur bonded to a benzyl group adsorbs to a copper plate, which is followed by the reaction as the second stage in which the sulfur compound reacts with copper to produce copper sulfide and also produce a benzyl radical and a benzyl sulfenyl radical.

The benzyl radicals produced at the second stage react with each other to produce bibenzyl. The benzil sulfenyl radical reacts with a hydrogen radical to produce benzyl mercaptan, reacts with a benzyl radical to produce dibenzyl sulfide, and reacts with another benzil sulfenyl radical to produce dibenzyl disulfide.

Among the above-described compounds, benzyl mercaptan is readily oxidized to dibenzyl disulfide under the environment in which copper coexists therewith as in the transformer, and becomes indistinguishable from the original compound, and therefore, is not suitable for diagnosis. Similarly, dibenzyl disulfide is also not suitable for diagnosis of the copper sulfide that is already produced within the transformer. Accordingly, bibenzyl and dibenzyl sulfide are suitable for diagnosis.

Bibenzyl and dibenzyl sulfide generated when these copper sulfides are produced can be detected by GC-MS.

The results of the experiments regarding production of bibenzyl and dibenzyl sulfide by the reaction between copper and a sulfur compound having sulfur bonded to a benzyl group will be hereinafter described in detail.

First, DBDS as an insulating oil containing a sulfur compound which is highly reactive with copper was dissolved in the alkylbenzene oil which is an insulating oil defined in JIS C 2320, class 2, No. 3, to prepare a sample oil. A reagent manufactured by Wako Junyaku KK was used for DBDS to adjust sulfur in the sample oil to have a mass concentration of 30 ppm.

Then, 5 grams of the sample oil and approximately 0.5 grams of a copper plate (a thickness of 0.2 mm) are enclosed in the sample bottle having a volume of 10 $cm^3$. The sample bottle is heated at 150° C. for a predetermined period of time. This heating accelerates the production of copper sulfide. Since the produced copper sulfide adheres to the surface of the copper plate, the amount of the produced copper sulfide can be obtained based on the difference of the weight of the copper plate between before and after heating.

Then, the concentration of each of bibenzyl and dibenzyl sulfide in the insulating oil is obtained by using a GC-MS device. The procedure will be hereinafter described in detail taking bibenzyl as an example. The heated sample oil is weighed out and diluted with hexane so as to allow the signal intensity appropriate for the GC-MS analysis to be obtained. Although hexane is used in this case, any other solvent in which alkylbenzene, bibenzyl and DBDS can readily be dissolved may be used. Then, 1 $mm^3$ of this solution is poured into the gas chromatograph.

The quantitative determination of bibenzyl and the like is carried out by the usual method using the peak area value of the gas chromatogram. The data analysis may be carried out based on a total ion chromatogram, or may be carried out using the peak area obtained by the selective ion monitoring method.

Figure 4:
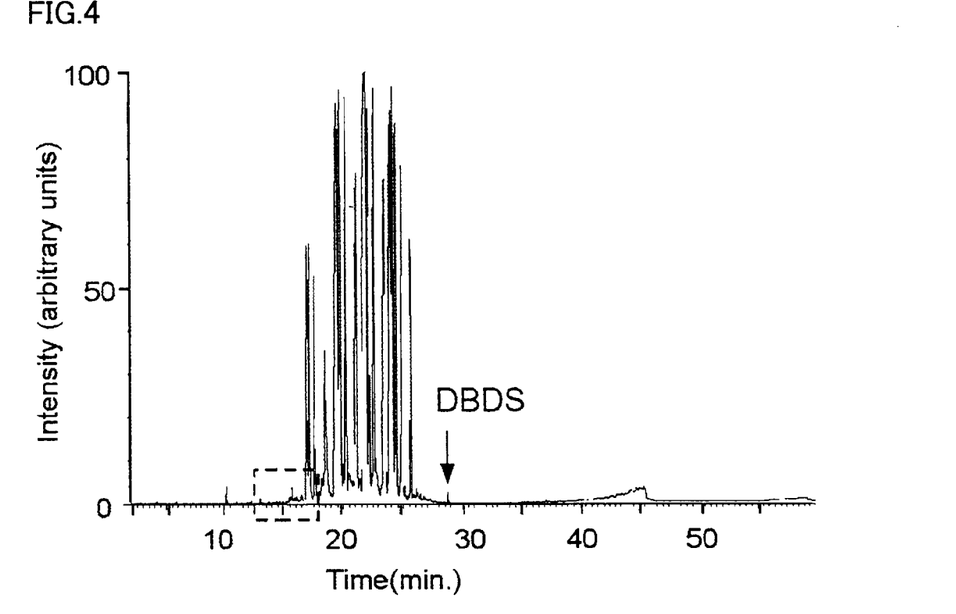
FIG. 4 is a graph showing the experimental results of the diagnostic method for the oil-filled electrical apparatus according to the second embodiment.
Figure 5:
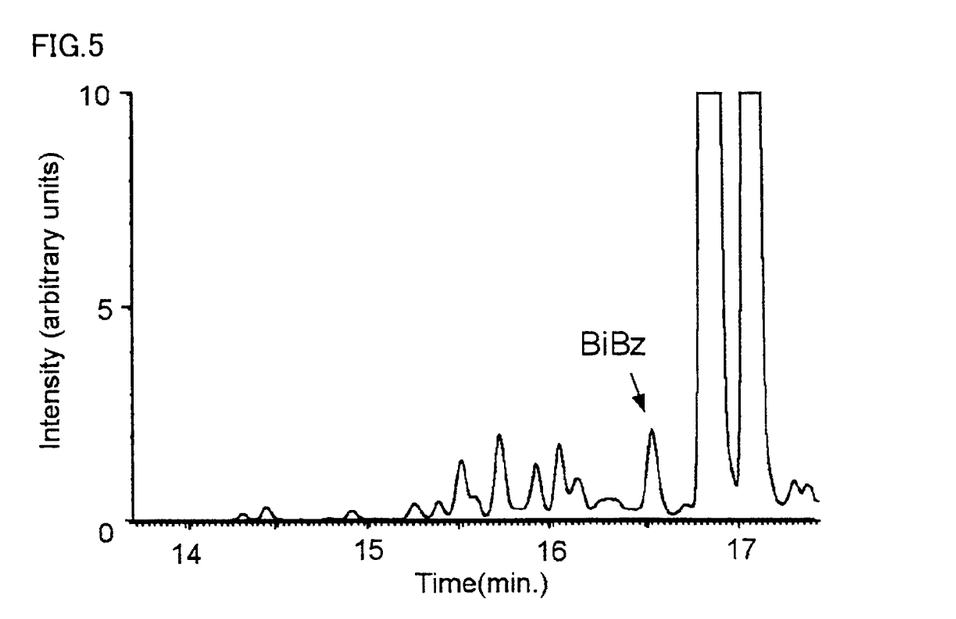
FIG. 5 is a graph showing the experimental results of the diagnostic method for the oil-filled electrical apparatus according to the second embodiment.

FIGS. 4 and 5 each are a graph showing the experimental results of the diagnostic method for the oil-filled electrical apparatus according to the second embodiment. FIGS. 4 and 5 each show a gas chromatogram of GC-MS. FIG. 5 is an enlarged view of the rectangular portion outlined by a dotted line in FIG. 4. FIG. 4 shows a peak of the added DBDS. FIG. 5 shows a peak BiBz of bibenzyl. The bibenzyl concentration in the oil can be calculated from this peak area and the weight of the sample oil. In addition, it is presumed that the peak of bibenzyl is formed due to the reaction between DBDS and copper since it does not appear in the case of the unused alkylbenzene oil or the alkylbenzene oil which is added with copper in place of DBDS and heated.

Figure 6:
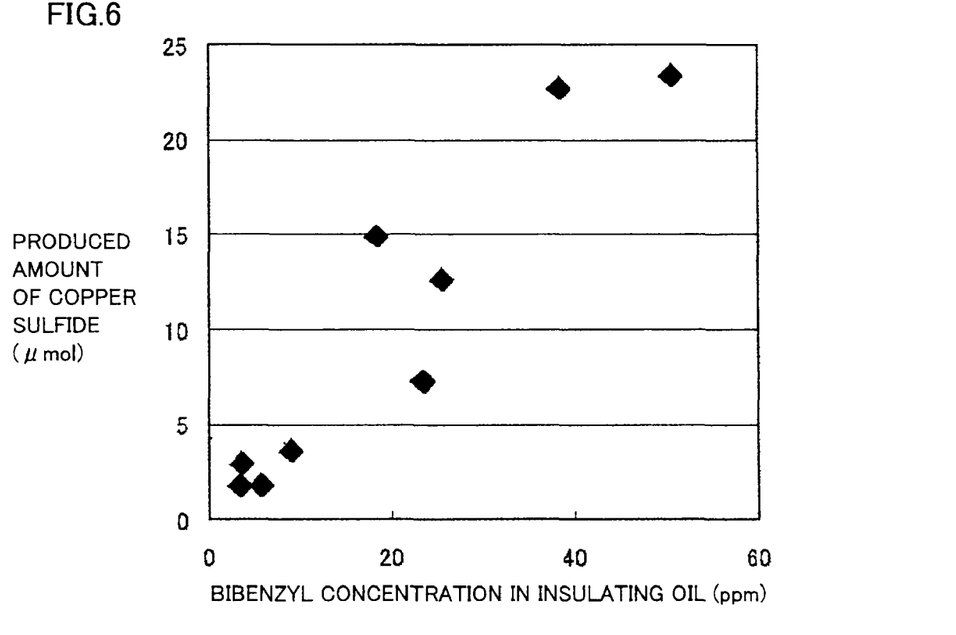
FIG. 6 is a graph showing the experimental results of the diagnostic method for the oil-filled electrical apparatus according to the second embodiment.

FIG. 6 is a graph showing the experimental results of the diagnostic method for the oil-filled electrical apparatus according to the second embodiment, and shows the relationship between the amount of bibenzyl in the insulating oil calculated by the above-described method and the amount of the produced copper sulfide calculated based on the mass variation of the copper plate. The figure shows that the concentration of bibenzyl in the insulating oil is approximately proportional to the produced amount of the copper sulfide. Accordingly, the produced amount of the copper sulfide can be estimated by determining a quantity of bibenzyl in the insulating oil.

Generally, bibenzyl is not contained in the unused insulating oil. Accordingly, when a small amount of the insulating oil is extracted from the exiting oil-filled electrical apparatus and bibenzyl is detected, it is assumed that copper sulfide is produced, to thereby allow diagnosis of a failure of the oil-filled electrical apparatus. Furthermore, dibenzyl sulfide can also be used for diagnosis of a failure of the oil-filled electrical apparatus in the same manner as in the case of bibenzyl.

Since bibenzyl and dibenzyl sulfide are generally not contained in the unused insulating oil, a failure diagnosis for the oil-filled electrical apparatus may be made by detecting these substances including bibenzyl and dibenzyl sulfide and also the sulfur compound having sulfur bonded to a benzyl group, simultaneously. If all of them are detected, it is presumed there is a higher possibility that copper sulfide is produced, which allows a diagnosis with a high degree of reliability.

The diagnostic method according to the second embodiment eliminates the need to detect in advance the compound in the insulating oil to be introduced into the oil-filled electrical apparatus, and to measure the temporal change of the amount of the compound. This facilitates a diagnosis for the existing oil-filled electrical apparatus.

On the other hand, it may be that the temporal change of the concentration of bibenzyl or dibenzyl sulfide in the unused insulating oil before introduced into the oil-filled electrical apparatus is measured to diagnose a failure of the oil-filled electrical apparatus based on the temporal change. It is considered that these compounds are increased in accordance with an increase in the amount of the produced copper sulfide since a sulfur compound is produced during the reaction with copper. Consequently, it is also possible to diagnose a failure by estimating the produced copper sulfide based on the variation amount of the concentration.

Third Embodiment

The third embodiment also provides a diagnostic method for the oil-filled electrical apparatus for diagnosing a failure by detecting a sulfur compound having sulfur bonded to a benzyl group and at least one compound of bibenzyl and dibenzyl sulfide, as in the above-described embodiments. The diagnostic method for the oil-filled electrical apparatus according to the third embodiment includes the steps of: contacting alumina or silica gel with an insulating oil; immersing the alumina or silica gel contacted with the insulating oil in the solvent; and analyzing, by a GC-MS method, the solvent in which the alumina or the silica gel is immersed, to detect bibenzyl or a sulfur compound having sulfur bonded to a benzyl group and diagnose a failure in accordance with a detected amount of the bibenzyl or the sulfur compound. The failure diagnosis may be carried out in accordance with the detected amount of each of the bibenzyl and the sulfur compound.

As shown in FIG. 3 of the first embodiment, when an oil defined in JIS C 2320, class 1, No. 4 is used as an insulating oil, in accordance with the GC-MS analysis, the position of the peak of the sulfur compound having sulfur bonded to a benzyl group, such as DBDS, overlaps the signal obtained based on the component contained in the insulating oil but not involved in production of copper sulfide. Furthermore, the signal also overlaps the peak position where bibenzyl is detected, which pauses a problem that the concentration of each of these substances cannot be detected when it is relatively low.

Thus, particularly in the case where a mineral oil is used as an insulating oil, it may be that bibenzyl and a sulfur compound having sulfur bonded to a benzyl group are separated in advance by an adsorbent from the component contained in the insulating oil but not involved in production of copper sulfide, and then subjected to analysis by gas chromatography-mass spectrometry. In this case, an alumina adsorbent or silica gel may be used as an adsorbent. An example in which an alumina adsorbent is used will be described below.

First, a sample oil is prepared by mixing DBDS into the insulating oil corresponding to a mineral oil defined in JIS C 2320, class 1, No. 4 and not containing sulfur causing copper sulfide so as to achieve sulfur to have a mass concentration of 30 ppm. A reagent manufactured by Wako Junyaku KK is used for DBDS. Then, 5 grams of the sample oil and a copper plate (a thickness of 0.2 mm, a mass of approximately 0.5 grams) are enclosed in a sample bottle having a volume of 10 cm$^3$. The sample bottle was heated at 150° C. for a predetermined period of time. This heating serves to produce copper sulfide. The amount of the produced copper sulfide can be obtained based on the mass variation of the copper plate between before and after heating.

Then, 200 mm$^3$ of the heated mineral oil and 200 mm$^3$ of hexane are mixed with each other and passed through a column filled with an alumina adsorbent. The alumina adsorbent filled therein is commercially available and has a particle size of approximately 10 to 100 microns. The column is filled with approximately 100 mg of an alumina adsorbent activated by the usual method.

While bibenzyl and dibenzyl sulfide are adsorbed to alumina and remain in the column, paraffin and naphthene each as a main component of the mineral oil are not adsorbed but flow out of the column. However, some paraffin and naphthene may remain, which can be removed by further washing the column with hexane.

Although washing with hexane should be sufficiently performed, if it is excessively performed, the intended substance such as bibenzyl and the like may also flow out. Thus, it is desirable to determine an appropriate amount of hexane for washing in advance in accordance with the properties of alumina such as its dryness.

Then, when the solvent such as toluene is passed through the column, an intended component can be collected in the solvent. The solvent used for elution is not limited to toluene, but may be liquid consisting only of dichloromethane, methanol or the like, and also may be a mixed solvent such as a toluene/hexane solution.

The solvent containing bibenzyl and the like obtained through the above-described procedure is subjected to the GC-MS analysis, to detect at least one of bibenzyl and a sulfur compound having sulfur bonded to a benzyl group, and diagnose a failure of the oil-filled electrical apparatus.

Figure 7:
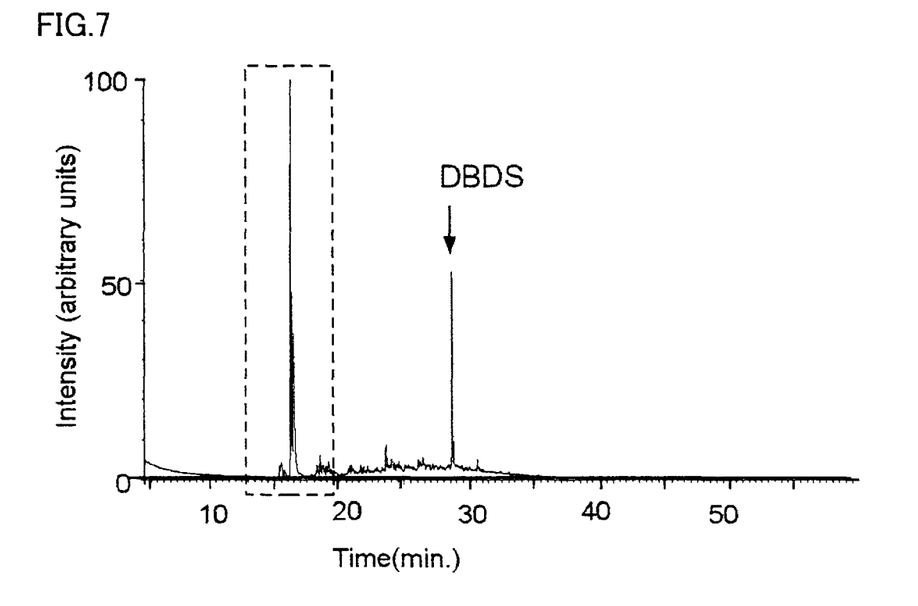
FIG. 7 is a graph showing the experimental results of the diagnostic method for the oil-filled electrical apparatus according to the third embodiment.
Figure 8:
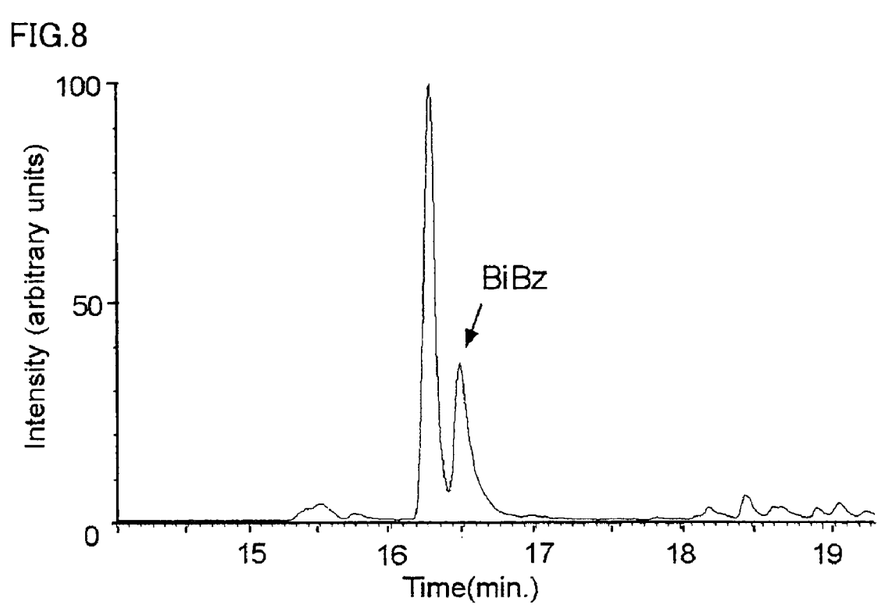
FIG. 8 is a graph showing the experimental results of the diagnostic method for the oil-filled electrical apparatus according to the third embodiment.

FIGS. 7 and 8 each are a graph showing the experimental results of the diagnostic method for the oil-filled electrical apparatus according to the third embodiment, and show a chromatogram of the toluene solution. FIG. 8 is an enlarged view of the portion outlined by a dotted line in FIG. 7. As comparing FIG. 7 with FIG. 3, it is shown that the signal of the component contained in the mineral oil but not involved in production of copper sulfide is decreased, and thus, the signal of DBDS can be clearly detected. In addition, peak BiBz of bibenzyl clearly appears in FIG. 8. In the case where the peak of another component contained in the mineral oil is relatively large as shown in FIG. 3, peak BiBz of bibenzyl cannot be detected.

Although alumina is used as an adsorbent in the above-described procedure, silica gel may also be used to achieve a similar effect of improving the detection accuracy. Furthermore, although it has been described that the detection accuracy for bibenzyl and DBDS is improved, the detection accuracy for dibenzyl sulfide as well as another sulfur compound having sulfur bonded to a benzyl group can also be improved.

In view of the foregoing, alumina or silica gel are contacted with the insulating oil, the alumina or silica gel contacted with the insulating oil is immersed in the solvent, and the solvent in which the alumina or silica gel is immersed is analyzed by a GC-MS method, to thereby detect bibenzyl or a sulfur compound having sulfur bonded to a benzyl group, with the result that the accuracy for detecting the bibenzyl and the sulfur compound is improved, which allows an accurate diagnosis of a failure of the oil-filled electrical apparatus.

The invention claimed is:

1. A diagnostic method for an oil-filled electrical apparatus for diagnosing a failure of the oil-filled electrical apparatus having a copper part disposed in an insulating oil, comprising:
chromatographically separating and detecting at least one compound of bibenzyl and dibenzyl sulfide in said insulating oil, and diagnosing a failure of said oil-filled electrical apparatus in accordance with a detected amount of said compound.

2. The diagnostic method for an oil-filled electrical apparatus according to claim 1, wherein a method for detecting a compound is implemented by gas chromatography-mass spectrometry.

3. A diagnostic method for an oil-filled electrical apparatus for diagnosing a failure of the oil-filled electrical apparatus having a copper part disposed in an insulating oil, comprising:
chromatographically separating and detecting a sulfur compound having sulfur bonded to a benzyl group in said insulating oil, and diagnosing a failure of said oil-filled electrical apparatus in accordance with a detected amount of said sulfur compound.

4. A diagnostic method for an oil-filled electrical apparatus for diagnosing a failure of the oil-filled electrical apparatus having a copper part disposed in an insulating oil, comprising:
chromatographically separating and detecting bibenzyl and a sulfur compound having sulfur bonded to a benzyl group in said insulating oil, and diagnosing a failure of said oil-filled electrical apparatus in accordance with a detected amount of said bibenzyl and said sulfur compound.

5. A diagnostic method for an oil-filled electrical apparatus for diagnosing a failure of the oil-filled electrical apparatus having a copper part disposed in an insulating oil, comprising:
contacting alumina or silica gel with the insulating oil;
immersing said alumina or said silica gel contacted with said insulating oil in a solvent; and
chromatographically separating and analyzing said solvent in which said alumina or said silica gel is immersed, to detect bibenzyl or a sulfur compound having sulfur bonded to a benzyl group, and diagnose a failure of said oil-filled electrical apparatus in accordance with a detected amount of said bibenzyl or said sulfur compound.

* * * * *